United States Patent [19]

Nakanishi et al.

[11] Patent Number: 4,876,372

[45] Date of Patent: Oct. 24, 1989

[54] METHOD FOR PREPARING EPICHLOROHYDRINS

[75] Inventors: Takehisa Nakanishi, Takaishi; Eizi Koga, Izumi; Isao Fukada, Takaishi, all of Japan

[73] Assignee: Mitsui Toatsu Chemicals, Incorporated, Tokyo, Japan

[21] Appl. No.: 181,181

[22] Filed: Apr. 13, 1988

[30] Foreign Application Priority Data

Apr. 16, 1987 [JP] Japan .................................. 62-91899
Feb. 4, 1988 [JP] Japan .................................. 63-22730

[51] Int. Cl.$^4$ ........................................... C07D 301/19
[52] U.S. Cl. ................................................... 549/529
[58] Field of Search ......................................... 549/529

[56] References Cited

U.S. PATENT DOCUMENTS 3,923,843 12/1975 Wulff et al. ......................... 549/529
4,021,454 3/1977 Wulff et al. ......................... 549/529

OTHER PUBLICATIONS

*Journal of Catalysis*, vol. 31, pp. 438–443, Mar. 13, 1973, "The Effects of Solvent & Hydroperoxide Structure" by Sheldon et al.
*Condensed Aromatics*, vol. 82, 1975; 31186n "Epoxidation of Allyl Chloride by Organic Hydroperoxides", by Dermer & Hodnett Tr. Mosk. Khim.-Tekhnol. Inst. 74 19–20 (1973).

Primary Examiner—Richard L. Raymond
Assistant Examiner—Mark W. Russell
Attorney, Agent, or Firm—Oblon, Spivak, McClelland, Maier & Neustadt

[57] ABSTRACT

The present invention is directed to a method for preparing epichlorohydrins by epoxidizing allyl chlorides with an organic hydroperoxide, and the epoxidation reaction is performed in the presence of a catalyst having titanium atoms bound to a silicon dioxide carrier and having silanol groups on the same carrier, whereby epichlorohydrins are obtained in high yield.

8 Claims, 1 Drawing Sheet

METHOD FOR PREPARING EPICHLOROHYDRINS

BACKGROUND OF THE INVENTION (1) Field of the Invention

The present invention relates to a method for preparing epichlorohydrins from allyl chlorides and an alkyl hydroperoxide.

(2) Description of the Prior Art

As manufacturing techniques of epichlorohydrins, there are known a chlorohydrin process, a chlorination process of allyl alcohol and a peroxide process.

In the chlorohydrin process, allyl chloride and chlorohydrin are used as a raw material and as an oxidizing agent, respectively, and therefore the amount of chlorine which is used therein is too great. In the allyl alcohol process mentioned above, a raw material is expensive. With regard to the aforesaid peroxide process, some manners are known in which tert-butyl hydroperoxide, ethylbenzene hydroperoxide, cumene hydroperoxide, hydrogen peroxide, a peracid and the like are used as oxidizing agents. In addition, there is a process of using a homogeneous catalyst, which is disclosed in Japanase Pat. Publication Nos. 19609/73 and 17649/70 and Tr. Mosk. Khim. Tekhnol. Inst., 74, p. 19–20 (1973). However, this process has the disadvantage that the recovery of the product is intricate and difficult, since the used catalyst is dissolved in the reaction product. There is another synthetic technique for epichlorohydrin in which epoxidation of propylene or allyl chloride is carried out with the aid of an alkyl hydroperoxide in the presence of a solid catalyst in order to synthesize the desired epichlorohydrin, and this synthetic technique is described in West German Pat. No. 2,334,315, U.S. Pat. No. 4,021,454 and J. Catalysis, 31, p. 438 (1973). In these publications, the reaction is performed by the use of the catalyst which has been prepared by first impregnating silica gel with titanium tetrachloride and then calcining it at 500° C. or more, preferably at 800° C.

In these publications, the reaction is performed by using stable tert-butyl hydroperoxide as the hydroperoxide and 2,6-di-tert-butyl-4-methylphenol as a stabilizer, so that epichlorohydrin is obtained in a selectivity of 73% (on the basis of the hydroperoxide). However, when ethylbenzene hydroperoxide is used, the selectivity is 55%, and in the case of the use of cumene hydroperoxide, the selectivity is no more than 8%. Therefore, it is difficult to manufacture epichlorohydrin on an industrial scale by these methods.

There has not been known the technique in which economically advantageous tert-butyl hydroperoxide, ethylbenzene hydroperoxide, cumene hydroperoxide or cyclohexyl hydroperoxide is used as an alkyl hydroperoxide in the presence of a heterogeneous solid catalyst without adding any antioxidant in order to epoxidize allyl chlorides, thereby producing epichlorohydrins in high selectivity.

In the above publications, the following is described: In allyl chlorides, the reactivity of a double bond is noticeably poor because of a high electron attractive force of a chlorine atom, so that the epoxidation reaction scarcely progresses, which results in useless decomposition of the hydroperoxide.

SUMMARY OF THE INVENTION

An object of the present invention is to provide a method for preparing epichlorohydrins from allyl chlorides in high conversion and in high selectivity, and according to this novel method, the above problems can be solved.

The inventors of the present application have intensively conducted research with the intention of solving the above-mentioned problems, and they have found that the employment of a catalyst in which titanium atoms and silanol groups are supported on a silicon dioxide carrier permits achieving the object of the present invention, and on the basis of this knowledge, the present invention has been completed.

That is, the present invention is directed to a method for preparing epichlorohydrins by reaction between allyl chlorides and an alkyl hydroperoxide in the presence of a catalyst having titanium atoms bound to a silicon dioxide carrier via oxygen atoms and having one or more silanol groups per square nanometer of the carrier.

According to the method of the present case, epichlorohydrins can be manufactured at low temperature from allyl chlorides in high conversion and selectivity by the use of an industrially available alkyl hydroperoxide as an oxidizing agent, and thus it is fair to say that the method of the present invention is extremely valuable in industrial fileds.

Figure 1:
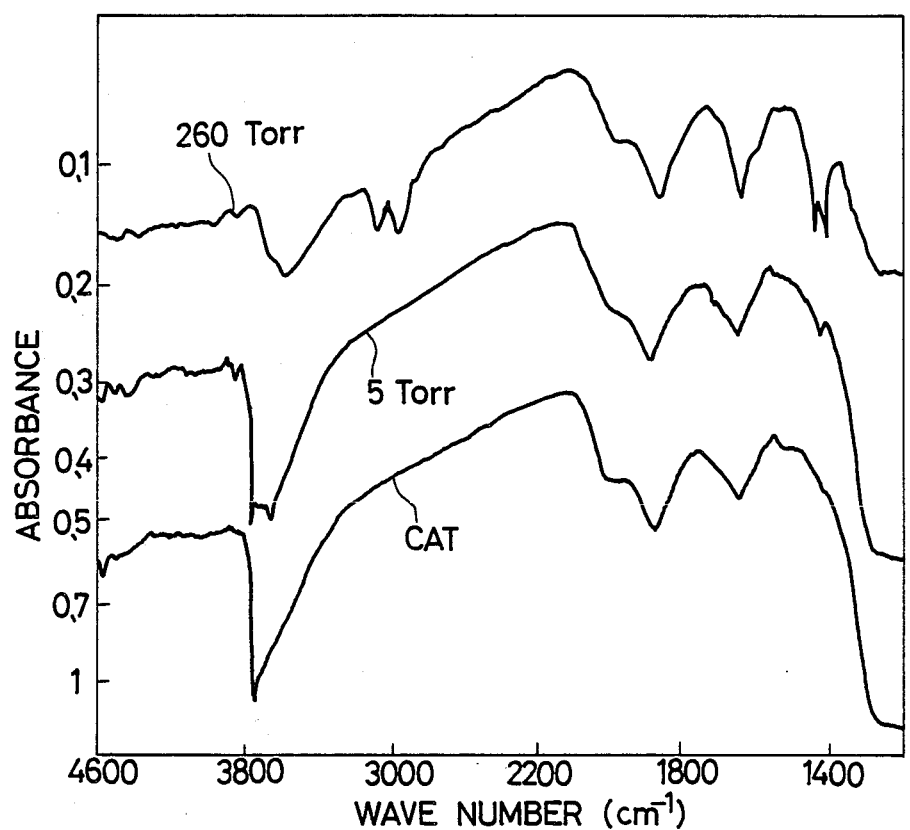
FIG. 1 is an infrared absorption spectrum analytical chart showing a state where allyl chloride of a raw material for reaction is adsorbed by silanol groups on a catalyst carrier in the present invention.

In this drawing, CAT represents an absorbance of the catalyst in which allyl chloride has not been adsorbed yet, 5 Torr represents an absorbance of the catalyst in which allyl chloride has been adsorbed under conditions of 5 Torr, and 260 Torr represents an absorbance of the catalyst in which allyl chloride has been adsorbed under conditions of 260 Torr.

DETAILED DESCRIPTION OF THE INVENTION AND PREFERRED EMBODIMENTS

In the present invention, allyl chlorides generically mean allyl chloride and 2-alkylallyl chloride in which a hydrogen atom at 2-position of allyl chloride is replaced with an alkyl group.

Furthermore, in the present invention, an alkyl hydroperoxide means cumene hydroperoxide, ethylbenzene hydroperoxide, tert-butyl hydroperoxide or cyclohexyl hydroperoxide.

Therefore, in the present invention, epichlorohydrins generically mean epichlorohydrin and 2-alkylepichlorohydrin which correspond to the above defined allyl chlorides.

A catalyst used in the present invention is a silicon dioxide carrier having titanium atoms bound to the carrier via oxygen atoms and having silanol groups on the same carrier. In general, this kind of catalyst can be prepared by bringing a titanium halide, an alkoxytitanium, a carbonyl compound of titanium, or the like into contact with a silica hydrogel having a suitable surface area and a suitable surface concentration of silanol groups, and then heating the hydrogel at such a low temperature as to leave the silanol groups thereon in an atmosphere of a non-reducing gas or an oxygen-containing gas. Alternatively, the catalyst regarding the present invention may be prepared by another process which comprises previously partially etherifying or esterifying the silanol surface of the carrier with an alcohol or an acid, causing the above-mentioned titanium compound to be supported on the carrier, and removing ether groups or ester groups therefrom to reproduce the silanol groups on the surface of the carrier. In addition, the catalyst of the present invention may be prepared by still another process which comprises previously dehydrating a silica carrier so that the surface of the carrier may have siloxane bonds, causing the above-mentioned titanium compound to be supported thereon, and then hydrating the carrier with a water vapor treatment or the like in order to impart a necessary number of silanol groups to the carrier surface.

The aforesaid silica hydrogel may be prepared by precipitation from sodium silicate, decomposition of a silicate, combustion of ethyl silicate, or another procedure. In the preferable silica hydrogel having the silanol groups on the surface thereof, a specific surface area is 1 m$^2$/g or more, preferably 100 m$^2$/g or more, a pore diameter is 50 Å or more, preferably 100 Å or more, a pore volume is 0.01 ml/g or more, preferably 0.1 ml/g or more, the number of the silanol groups on the surface is one or more, preferably 3 or more per square nanometer of the surface area (1 square nanometer = $10^{-18} m^2$).

With regard to the titanium compounds, liquid compounds are preferable on account of easy usage, and titanium tetrachloride, alkoxytitanium and the like are used. The silica hydrogel may be impregnated directly with the titanium compound, or alternatively the impregnation may be carried out after the titanium compound has been previously diluted with a solvent such as an hydrocarbon or an alcohol.

In order to cause the silica gel to support the titanium compound, the former is brought into contact with the latter in a non-active atmosphere. Afterward, the used solvent is removed therefrom by heating the gel under atmospheric pressure or under reduced pressure, and the silica gel is further heated usually at a temperature in the range of 100° C. to 500° C., preferably at a temperature in the range of 120° C. to 250° C. in an atmosphere of a non-reducing gas such as nitrogen, argon or carbon dioxide, or an oxygen-containing gas such as air, in order to prepare the desired catalyst.

A period of time necessary for the above heating treatment is 0.5 to 10 hours, usually 1 to 5 hours. The temperature and the time for the heat treatment have a great influence on the number of the silanol groups on the carrier, and therefore these conditions are very important in the manufacture of the catalyst.

In the catalyst obtained in the above manner, titanium atoms are bound to silicon atoms via oxygen atoms, and the concentration of titanium is 0.01 to 20 titanium atoms, preferably 0.5 to 9 titanium atoms per square nanometer of a specific surface area. In the case of the carrier having a specific surface area of 100 m$^2$/g, the number of 0.5 to 9 titanium atoms per square nanometer is comparable to a concentration of 0.4 to 7 wt %/g of the supported titanium atoms. The hydroperoxide is activated when coordinated with the titanium atoms.

On the other hand, the allyl chlorides have a low selectivity toward an epoxide, since the electronegativity of a chlorine atom is high and thus the reactivity of a double bond is poor. For example, when allyl chloride is epoxidized with ethylbenzene hydroperoxide, epichlorohydrin is prepared in a selectivity of 55%, but when cumene hydroperoxide is used, the selectivity is no more than 8%.

However, in the case that the catalyst of the present invention is used, it has been found that the allyl chlorides are adsorbed by the silanol groups on the surface of the catalyst, so that the reaction makes progress in high conversion and in high selectivity. Moreover, the epoxidation reaction characteristically takes place at an extremely low temperature, and it is considered that in this epoxidation, the allyl chlorides adsorbed by the silanol groups are reacted with the hydroperoxide coodinated with titanium.

Infrared absorption spectrum elucidates that allyl chloride is adsorbed by the silanol groups. FIG. 1 shows examples of infrared absorption spectra of the catalyst (CAT) regarding the present invention and catalysts on which allyl chloride was adsorbed at 5 Torr and 260 Torr, and amounts of adsorbed allyl chloride at 5 Torr and 260 Torr were 0.15 mmol/g and 1.75 mmol/g, respectively, when measured by an adsorption weight balance method. The infrared absorption spectra clearly indicate that the absorption at 3,500 to 3,800 cm$^{-1}$ assigned to an Si-OH bond changes owing to the adsorption of allyl chloride.

The amount of the adsorbed allyl chloride depends upon the number of the silanol groups on the catalyst, and therefore it can be presumed that the catalyst of the present invention having the above-mentioned specific surface area and silanol density functions more effectively than conventional catalysts.

The number of the silanol groups on the catalyst surface is dependent upon the heat temperature in the non-reducing gas atmosphere. The higher the heating temperature is, the smaller the number of the silanol groups left thereon is. Accordingly, if the temperature for the heat treatment is high, the amount of the adsorbed allyl chloride decreases, and the yield of epichlorohydrin also deteriorates. This fact will be clarified in examples given below.

In the case that in the present invention, the alkyl hydroperoxide is reacted with the allyl chlorides in the presence of the catalyst in which the titanium atoms and the silanol groups are supported on the silicon dioxide carrier, these materials may be diluted with a solvent, if desired. Examples of the suitable solvents include ethylbenzene and cumene which are unreacted raw materials in manufacturing the hydroperoxide, and chlorinated alkane compounds, methylphenylcarbinol, dimethylphenylcarbinol, cyclohexanol and tert-butanol which are produced from the hydroperoxides. The concentration of the hydroperoxide is not particularly limited but is usually in the range of 5 to 90%.

The ratio of the allyl chlorides to the hydroperoxide is preferably high, and in general, the allyl chlroides are used in an amount of 2 moles or more, preferably 5 moles or more with respect to 1 mole of the hydroperoxide, whereby the yield can be improved.

However, even if the molar ratio of the allyl chlorides is extraordinarily raised, the yield cannot exceed a certain level. In consequence, 50 molar ratio or less is reasonable from an economical viewpoint.

The reaction may be performed in a batch system or a continuous system. The catalyst may be used in the state of a suspension or a fixed-bed. The amount of the catalyst is 0.01% by weight or more, preferably in the range of 0.05 to 30% by weight based on the weight of the hydroperoxide. Reaction temperature is usually in the range of 0° to 250° C., preferably 20° to 150° C.

When the reaction temperature is less than 0° C., reaction rate is too late, and when it is in excess of 250° C., the hydroperoxide decomposes selectively. Pressure for the reaction is not particularly limited, and any pressure is acceptable on condition that a reaction system is maintained in a liquid phase under the pressure.

EXAMPLE

Now, the present invention will be described in detail by way of examples.

(Preparation and Properties of Catalysts)

At 25° C., 2,170 g of a 30% aqueous sodium silicate solution was mixed with 27% sulfuric acid, and reaction was then performed at a pH of 1.5 for 1.5 hours in order to obtain a silica sol, and the latter was allowed to stand for 1.5 hours, so that gelation took place. The thus obtained gel was washed with ammonia water having a pH of 10.5 and was successively washed with water repeatedly, until the content of Na had reached a level of 0.05% or less. Then, this gel was dried at 150° C. overnight thereby preparing a silica hydrogel having a particle size of 32–120 mesh.

With regard to this silica hydrogel, a surface area was 300 m$^2$/g, an average pore diameter was 140 Å, and according to the results of thermogravimetric analysis, the number of silanol groups on the surface thereof was 6.0 per square nanometer.

Sixty grams of this silica hydrogel was added to a mixed solution of 120 ml of ethanol and 2.38 g of titanium tetrachloride, and the mixture was then stirred for 30 minutes so that the silica gel might be impregnated therewith. Ethanol was distilled off under atmospheric pressure, and the gel was then dried at 100° C. under a reduced pressure of 3 Torr for 1 hour.

On the thus obtained carrier, 0.42 titanium atom per square nanometer of its surface was supported.

The carriers prepared in the above manner were further heated at different temperatures in air stream for 2 hours in order to obtain catalysts A to F. The catalysts E and F were outside of the present invention and were used as comparative examples.

The following table exhibits temperatures of the heat treatment, numbers of surface silanol groups and amounts of allyl chlorides for the respective catalysts.

The numbers of the SiOH groups were each calculated from an amount of water decreased by heating the catalyst in accordance with a thermogravimetric analysis TG/DTA, and the amounts of the adsorbed allyl chlorides were sought in accordance with an adsorption weight balance method under conditions of an adsorption temperature of 25° C. and an adsorption pressure of 6 Torr.

| Catalyst | Temp. of Heat Treatment (°C.) | Number of SiOH Groups per nm$^2$ | Amount of Adsorbed Allyl Chloride (mmol/g) |
|---|---|---|---|
| A | 150 | 4.5 | 0.19 |
| B | 200 | 4.1 | 0.17 |
| C | 350 | 1.9 | 0.08 |
| D | 500 | 1.3 | 0.06 |
| E | 800 | 0.2 | 0.02 |
| F | 1000 | 0.05 | 0.02 |

EXAMPLE 1 AND COMPARATIVE EXAMPLE 1

In a 300-ml stainless steel autoclave were placed 12.0 g of each of the above-mentioned catalysts, 128.5 g of allyl chloride and 30.5 g of a cumene hydroperoxid solution containing 40% by weight of cumene hydroperoxide in cumene, and reaction was then performed at 80° C. for 5 hours. Concentrations of the remaining hydroperoxide in the resulting reaction mass were sought by means of an iodometry method, and conversions of cumene hydroperoxide were calculated. Yields of epichlorohydrin were also calculated from analytical results of gas chromatography. The results are set forth in Table 1.

TABLE 1

| | Catalyst | Conversion of CHP (%) | Yield of ECH (%) |
|---|---|---|---|
| Example 1 | A | 98 | 63 |
| | B | 99 | 62 |
| | C | 96 | 57 |
| | D | 94 | 35 |
| Comp. Example 1 | E | 90 | 17 |
| | F | 87 | 10 |

Notes:
CHP: Cumene hydroperoxide
ECH: Epichlorohydrin

EXAMPLE 2 AND COMPARATIVE EXAMPLE 2

In a 200-ml stainless steel autoclave were placed 12.0 g of each of the above-mentioned catalysts, 60 g of allyl chloride and 48 g of an ethylbenzene solution of 25% ethylbenzene hydroperoxide, and reaction was performed at 90° C. for 4 hours. Analysis was carried out in the same manner as in Example 1, and conversions of ethylbenzene hydroperoxide and yields of epichlorohydrin were sought. The above reaction was performed for the respective catalysts A, B, D, E and F. The results are set forth in Table 2.

TABLE 2

| | Catalyst | Conversion of EBHP (%) | Yield of ECH (%) |
|---|---|---|---|
| Example 2 | A | 97 | 81 |
| | B | 97 | 78 |
| | D | 95 | 63 |
| Comp. Example 2 | E | 92 | 49 |
| | F | 88 | 33 |

Note:
EBHP: Ethylbenzene hydroperoxide

EXAMPLE 3 AND COMPARATIVE EXAMPLE 3

In a 200-ml stainless steel autoclave were placed 12.0 g of each of catalysts B and E, 120 g of allyl chloride and 15 g of a tert-butanol solution of 80% tert-butyl hydroperoxide, and reaction was performed at 80° C. for 4 hours in order to epoxidize allyl chloride. The results are set forth in Table 3.

TABLE 3

| | Catalyst | Conversion of TBHP (%) | Yield of ECH (%) |
|---|---|---|---|
| Example 3 | B | 97 | 78 |
| Comp. Example 3 | E | 90 | 58 |

Note:
TBHP: tert-Butyl hydroperoxide

EXAMPLE 4 AND COMPARATIVE EXAMPLE 4

In a 300-ml stainless steel autoclave were placed 12.0 g of each of catalysts B and E, 120 g of 2-methylallyl chloride and 30 g of a cumene solution of 40% cumene hydroperoxide, and reaction was performed at 80° C. under a pressure of 1.5 kg/cm²G for 5 hours. The results are set forth in Table 4.

TABLE 4

| Catalyst | Conversion of CHP (%) | Yield of 2-MECH (%) |
|---|---|---|
| Example 4 | B | 94 | 80 |
| Comp. Example 4 | E | 87 | 55 |

Note:
2-MECH: 2-Methylepichlorohydrin

EXAMPLE 5 AND COMPARATIVE EXAMPLE 5

In a 300-ml stainless steel autoclave were placed 12.0 g of each of catalysts B and E, 120 g of allyl chloride and 120 g of a cyclohexane solution of 10% cyclohexyl hydroperoxide, and reaction was performed at 100° C. for 6 hours. The results are set forth in Table 5.

TABLE 5

| Catalyst | Conversion of CHXHP (%) | Yield of ECH (%) |
|---|---|---|
| Example 5 | B | 98 | 56 |
| Comp. Example 5 | E | 86 | 27 |

Note:
CHXHP: Cyclohexyl hydroperoxide

EXAMPLE 6

In a 300-ml glass four-necked flask were placed 12 g of the catalyst B, 120 g of allyl chloride and 30 g of a cumene solution of 40% cumene hydroperoxide, and reaction was then performed at 40° C. under atmospheric pressure for 10 hours.

According to analytical results of the resulting reaction mass, the conversion of cumene hydroperoxide was 93%, and the yield of epichlorohydrin was 69%.

What is claimed is:

1. A method for preparing epichlorohydrins, which comprises:

reacting a 2-alkylallyl chloride, wherein the alkyl substituent contains from 1 to 3 carbon atoms, with an alkyl hydroperoxide in the presence of a catalyst having titanium atoms bound to a silicon dioxide carrier via oxygen atoms and having at least three but not more than 6 silanol groups per square nanometer of the carrier, said catalyst having been heat treated at a temperature ranging from 100° C. to 250° C.

2. The method according to claim 1 wherein said alkyl hydroperoxide is one selected from the group consisting of cumene hydroperoxide, ethylbenzene hydroperoxide, tert-butyl hydroperoxide and cyclohexyl hydroperoxide.

3. The method according to claim 1, wherein said 2-alkylallyl chloride is allyl chloride or methallyl chloride.

4. The method according to claim 1, wherein said heat treatment is conducted in an atmosphere of a non-reducing gas.

5. The method according to claim 1, wherein the concentration of titanium atoms on the surface of the carrier ranges from 0.01 to 20 titanium atoms per square nanometer of specific surface area.

6. The method according to claim 5, wherein said surface concentration of titanium atoms range from 0.5 to 9.

7. The method according to claim 1, wherein the ratio of said 2-alkylallyl chloride to hydroperoxide reactant during the reaction ranges from 2 moles or more per one mole of hydroperoxide.

8. The method according to claim 1, wherein said reaction occurs at a temperature ranging from 120° to 250° C.